(12) United States Patent
Sakuta et al.

(10) Patent No.: US 6,258,347 B1
(45) Date of Patent: Jul. 10, 2001

(54) FILM-FORMING SILICONE COMPOSITION AND TOILETRY COMPOSITION CONTAINING SAME

(75) Inventors: Koji Sakuta; Hisashi Aoki, both of Gunma-ken (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 09/088,056

(22) Filed: Jun. 1, 1998

(30) Foreign Application Priority Data

Jun. 2, 1997 (JP) .................................................. 9-143802

(51) Int. Cl.[7] .............................. A61K 7/06; A61K 7/42; C08L 83/04; C08L 83/08
(52) U.S. Cl. ..................... 424/70.12; 424/401; 424/70.1; 424/70.11; 424/70.9; 424/59; 424/64; 514/63
(58) Field of Search .................... 424/401, 70.1, 424/70.11, 70.12, 70.9, 59, 64, 70.21, 70.22, 70.27, 70.31; 514/881, 63; 524/837

(56) References Cited

U.S. PATENT DOCUMENTS

| 5,154,915 | * 10/1992 | Weber et al. . | |
| 5,286,476 | 2/1994 | Nanba et al. | 424/47 |
| 5,567,426 | 10/1996 | Nadaud et al. | 424/401 |
| 5,800,816 | 9/1998 | Brevia et al. | 424/63 |
| 5,911,974 | 6/1999 | Brevia et al. | 424/65 |
| 5,965,112 | 10/1999 | Brevia et al. | 424/64 |

FOREIGN PATENT DOCUMENTS

| 0709 083 | 1/1996 | (EP) . |
| 0 829 254 | * 3/1998 | (EP) . |
| 94/21224 | * 9/1994 | (WO) . |
| 97/30681 | * 8/1997 | (WO) . |
| 97/30682 | * 8/1997 | (WO) . |

OTHER PUBLICATIONS

Patent Abstracts of Japan vol. 15,No. 068 (C–0807), Feb. 18, 1991 JP 02 295912 A (Shiseido Co. Ltd).

* cited by examiner

Primary Examiner—Thurman K. Page
Assistant Examiner—Brian K. Seidleck
(74) Attorney, Agent, or Firm—Millen, White, Zelano & Branigan, P.C.

(57) ABSTRACT

Provided by the invention is a film-forming silicone-based composition suitable as an additive ingredient in toiletry or cosmetic preparations or, in particular, in hair care treatment compositions such as shampoos to impart the treated hair with excellent glossiness and slipperiness along with excellent water and perspiration resistance. The composition comprises (A) a diorganopolysiloxane of a high degree of polymerization having fluorinated alkyl groups, optionally, in combination with amino- or ammonium-containing organic groups and (B) an oily constituent selected from (B1) a linear diorganopolysiloxane of a relatively low degree of polymerization, (B2) a cyclic diorganosiloxane oligomer and (B3) an isoparaffin oil having a specified boiling point. The silicone-based composition is formulated in a toiletry preparation together with a surface agent and water and/or ethyl alcohol.

19 Claims, No Drawings

FILM-FORMING SILICONE COMPOSITION AND TOILETRY COMPOSITION CONTAINING SAME

BACKGROUND OF THE INVENTION

The present invention relates to a novel film-forming silicone composition capable of forming a coating film on a substrate having excellent water resistance, perspiration resistance, oil resistance, glossiness and slipperiness and suitable as an additive ingredient in a cosmetic or toiletry preparation as well as a cosmetic or toiletry composition formulated therewith.

It is widely practiced in the prior art to formulate a toiletry preparation, in particular, for hair care treatment such as shampoos and hair rinses, with a silicone, i.e. organopolysiloxane, oil with an object to impart the hair with glossiness and slipperiness. As is disclosed in Japanese Patent Publication 7-29906, Japanese Patent Kokai 63-183517, 63-222109, 63-243018, 63-316713, 64-13012, 64-13013, 64-43342 and 1-272513 and elsewhere, formulation of a hair care treatment composition such as shampoos, rinses, hair treatments and hair conditioners with a silicone oil of high degree of polymerization has an effect to improve smoothness of combing or brushing and to prevent damages on the hair such as splitting. Japanese Patent Kokai 5-85918 also teaches that a protection of hair and improved sustainability of the effect can be obtained by the admixture of a hair care preparation with a silicone oil of high degree of polymerization having amino groups or ammonium groups in the molecular structure. The effectiveness of the silicone oils disclosed in the above mentioned prior art, however, is not quite satisfactory so that it is eagerly desired to develop a novel silicone-based film-forming composition capable of exhibiting further improved protection on hairs, i.e. oil resistance and slipperiness.

On the other hand, as is disclosed in Japanese Patent Publications 6-15448 and 6-15452 and Japanese Patent Kokai 61-161209, 61-161211, 62-298511, 62-298512, 62-298518 and 62-298519, film-forming silicone resins are used as an additive in skin care preparations and makeup preparations with an object to prevent collapsing of makeup by perspiration. A problem to be solved in connection with the use of a silicone resin is that users of such a preparation sometimes feel stickiness or stiffness on their skin treated therewith. In place of the above mentioned silicone resins, silicone oils of high degree of polymerization are also used in the same applications, as is taught in Japanese Patent Kokai 63-183515 and 63-183516, but such a formulation is inferior in respect of water resistance of the coating film as compared with the silicone resin-formulated preparations.

Further, Japanese Patent Kokai 7-233027 proposes use of a silicone resin having fluorine-substituted alkyl groups in the molecular structure as an additive in skin care and makeup preparations. Although an improvement can be obtained thereby in the water resistance, the problem of stickiness and stiffness of the skin treated with the preparation, as an inherence of silicone resin-formulated preparations, remains still unsolved.

A proposal is made in Japanese Patent Kokai 3-128311, 3-128312, 3-128909, 3-170518, 4-36218, 4-175318 and 4-359912 for the use of an acrylic silicone copolymer as an additive in toiletry and cosmetic preparations. A hair care treatment composition formulated with such a copolymeric silicone, however, is inferior in hair conditionability as compared with an ordinary silicone oil of a high degree of polymerization though excellent in the hair styling performance. When a skin care or makeup preparation is admixed with the copolymeric silicone, as is disclosed in Japanese Patent Kokai 2-25411, the problem of stickiness and stiffness of the skin treated therewith, like the formulations with a silicone resin, must be solved although such a preparation forms a film having good water resistance.

SUMMARY OF THE INVENTION

The present invention accordingly has an object, in view of the above mentioned problems in the conventional film-forming silicone materials as an additive in toiletry and cosmetic preparations, to provide a novel and improved silicone-based film-forming composition capable of forming a film having excellent water resistance, oil resistance and lubricity or slipperiness and imparting a toiletry or cosmetic preparation compounded therewith with excellent softness and glossiness as an inherent advantage of silicone oils of high degree of polymerization without the disadvantage of stickiness and stiffness on the skin treated therewith.

Thus, the film-forming silicone composition according to the invention is a uniform mixture which comprises:

(A) from 0.5 to 80% by weight of an organopolysiloxane of a high degree of polymerization which is a diorganopolysiloxane having a straightly linear molecular structure represented by the general formula

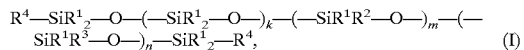

in which $R^1$ is an alkyl group, cycloalkyl group or aryl group having 1 to 20 carbon atoms, $R^2$ is a fluorine-substituted alkyl group having 1 to 15 carbon atoms, $R^3$ is an amino- or ammonium-functional organic group represented by the formula $-R^5Z$, $R^5$ being an alkylene group having 2 to 6 carbon atoms and Z being a group of the formula $-NR^6_2$, $-N^+R^6_3A^-$, $-NR^6(CH_2)_aNR^6_2$ or $-NR^6(CH_2)_aN^+R^6A^-$ with the proviso that $R^6$ is a hydrogen atom or an alkyl group having 1 to 4 carbon atoms, A is a halogen atom and the subscript a is an integer of 2 to 6, $R^4$ is $R^1$, $R^2$, $R^3$ or a hydroxyl group, the subscripts k and m are each, independently from the other, a positive integer and the subscript n is 0 or a positive integer with the proviso that k+m+n is in the range from 2000 to 20,000, of which the content of nitrogen does not exceed 1% by weight and the content of fluorine is in the range from 1% to 50% by weight; and (B) from 20 to 99.5% by weight of an oily compound selected from the group consisting of:

(B1) a diorganopolysiloxane having a straightly linear molecular structure represented by the general formula

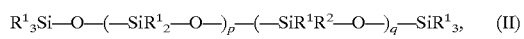

in which $R^1$ and $R^2$ each, independently from the other, have the same meaning as defined above and the subscripts p and q each, independently from the other, are 0 or a positive integer not exceeding 500 with the proviso that p+q does not exceed 500, and having a viscosity not exceeding 1000 centistokes at 25° C.;

(B2) a cyclic diorganosiloxane oligomer represented by the general formula

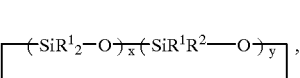

in which $R^1$ and $R^2$ each, independently from the other, have the same meaning as defined above and the subscripts x and y are each, independently from the other, 0 or a positive integer not exceeding 7 with the proviso that x+y is a positive integer in the range from 3 to 7; and (B3) an isoparaffin hydrocarbon compound having a boiling point in the range from 60 to 260° C. under normal pressure, the total amount of the components (A) and (B) being 100% by weight.

The invention further provides a hair care treatment composition which comprises:

(a) from 0.1 to 50% by weight of a surface active agent;
(b) from 0.1 to 20% by weight of the film-forming silicone composition defined above; and
(c) from 1 to 95% by weight of water, ethyl alcohol or a combination thereof.

DETAILED DESCRIPTION OF THE PREFERRED EMBODIMENTS

In the above defined film-forming silicone composition of the invention, the high-molecular diorganopolysiloxane as the component (A) is the film-forming ingredient and represented by the general formula (I) given above. In the general formula (I), $R^1$ is an alkyl group, cycloalkyl group or aryl group having 1 to 20 carbon atoms, $R^2$ is a fluorine-substituted alkyl group having 1 to 15 carbon atoms, $R^3$ is an amino- or ammonium-functional organic group represented by the formula —$R^5Z$, $R^5$ being an alkylene group having 2 to 6 carbon atoms and Z being a group of the formula —$NR^6{}_2$, —$N^+R^6{}_3A^-$, —$NR^6(CH_2)_aNR^6{}_2$ or —$NR^6(CH_2)_aN^+R^6A^-$ with the proviso that $R^6$ is a hydrogen atom or an alkyl group having 1 to 4 carbon atoms, and A is a halogen atom and the subscript a is an integer of 2 to 6, and $R^4$ is $R^1$, $R^2$, $R^3$ or a hydroxyl group. The subscripts k and m are each, independently from the other, a positive integer and the subscript n is 0 or a positive integer with the proviso that k+m+n is in the range from 2000 to 20,000. It is essential that the content of nitrogen does not exceed 1% by weight and the content of fluorine is in the range from 1% to 50% by weight in the diorganopolysiloxane as the component (A). When the component (A) contains the groups denoted by A which are each a fluorine atom, the above mentioned content of fluorine in the component (A) is calculated by including the fluorine atoms as the groups A.

The group denoted by $R^1$ is exemplified by alkyl groups such as methyl, ethyl, propyl, butyl, pentyl, hexyl, heptyl, octyl, nonyl, decyl, myristyl, cetyl and stearyl groups, cycloalkyl groups such as cyclopentyl and cyclohexyl groups and aryl groups such as phenyl and tolyl groups. It is preferable that all or at least 90% of the groups denoted by $R^1$ in the component (A) are methyl groups, the balance, if any, being phenyl groups.

The group denoted by $R^2$ is a fluorine-substituted alkyl group which is preferably a 2-(perfluoroalkyl)ethyl or 3-(perfluoroalkyl)propyl group exemplified by those expressed by the formulas —$CH_2CH_2CF_3$, —$CH_2CH_2C_4F_9$, —$CH_2CH_2C_8F_{17}$, —$CH_2CH_2C_{10}F_{21}$, —$CH_2CH_2CH_2CF_3$, —$CH_2CH_2CH_2C_4F_9$, —$CH_2CH_2CH_2C_8F_{17}$, —$CH_2CH_2CH_2C_{10}F_{21}$ and —$CH_2CH_2CH_2C(C_4F_9)_2C_3F_7$, of which 2(perfluoromethyl)ethyl and 3-(perfluorooctyl) propyl groups are preferable.

The group denoted by $R^3$ in the general formula (I) is an amino- or ammonium-functional organic group generally expressed by the formula —$R^5Z$, in which $R^5$ is an alkylene group having 2 to 6 carbon atoms and Z is a group expressed by the formula —$NR^6{}_2$, —$N^+R^6{}_3A^-$, —$NR^6(CH_2)_aNR^6{}_2$ or —$NR^6(CH_2)_aN^+R^6A^-$ in which $R^6$ is a hydrogen atom or an alkyl group having 1 to 4 carbon atoms, A is a halogen atom such as chlorine, bromine and iodine atoms and the subscript a is an integer of 2 to 6. Preferably, the group $R^3$ is a 3-aminopropyl group of the formula —$CH_2CH_2CH_2NH_2$ or 3-N-(2-aminoethyl)aminopropyl group of the formula —$CH_2CH_2CH_2NHCH_2CH_2NH_2$.

In the general formula (I), the subscripts k and m are each a positive integer and the subscript n is 0 or a positive integer with the proviso that k+m+n is in the range from 2000 to 20000 or, preferably, from 2500 to 10000. When the value of k+m+n is too small, the strength of the film formed from the composition cannot be high enough so that the hair care treatment preparation prepared from the composition cannot exhibit good protective effects on the hair treated therewith while, when the value of k+m+n is too large, a decrease is caused in the miscibility of the component (A) with the component (B) resulting in a difficulty in the preparation of the toiletry compositions.

When the subscript n is 0 and the group denoted by $R^4$ is not $R^3$, the diorganopolysiloxane as the component (A) is characterized by the fluorine-substituted alkyl groups denoted by $R^2$ while, when the subscript n is not 0, the diorganopolysiloxane as the component (A) is characterized by both of the fluorine-substituted alkyl groups $R^2$ and the amino- or ammonium-functional organic groups $R^3$. Although a film-forming silicone composition improved in the water resistance, oil resistance and slipperiness retaining the softness and glossiness as the inherency of high-molecular silicone oils can be obtained even in the former case, i.e. when the component (A) is free from the amino- or ammonium-functional organic groups $R^3$, it is preferable that n is not 0 in respect of obtaining good sustainability of these advantageous effects.

It is essential that the content of nitrogen in the diorganopolysiloxane as the component (A) does not exceed 1% by weight or, preferably, does not exceed 0.5% by weight. When the nitrogen content therein is too high, i.e. when the content of the amino or ammonium groups is too high, the composition formulated therewith is disadvantageous in respect of a lastingly emitted unpleasant odor and discoloration.

The content of fluorine in the component (A) is in the range from 1 to 50% by weight or, preferably, from 1 to 20% by weight. When the content of fluorine is too low, no improvement can be obtained in the oil resistance and slipperiness of the composition while, when the content of fluorine is too high, a decrease is caused in the miscibility of the component (A) with the component (B). When the fluorine content in the component (A) is in the range from 20 to 50% by weight, in particular, it is preferable that the component (B) is selected from linear or cyclic diorganopolysiloxanes, i.e. components (B1) and (B2), of which the organic groups are fluorine-substituted alkyl groups in order to ensure good miscibility between the components (A) and (B).

The method for the preparation of the high-molecular dimethylpolysiloxane as the component (A) is known in the art. Namely, starting oligomeric dimethyl siloxanes containing and not containing fluorine atoms and amino or ammonium groups including low-molecular linear dimethylpolysiloxane, cyclic dimethylpolysiloxane, linear dimethylpolysiloxane having fluorine-substituted alkyl groups, cyclic dimethylpolysiloxane having fluorine-substituted alkyl groups, amino group-containing dimethylpolysiloxane and hexamethyl disiloxane are blended together in a specified proportion and they are subjected to a polymerization reaction in the presence of an alkaline catalyst.

The component (B) is an oily material which serves to dissolve the above described component (A) as the film-forming ingredient and selected from the group consisting of three classes of compounds including (B1) silicone oils of a linear molecular structure represented by the general formula (II), (B2) silicone oils having a cyclic molecular structure represented by the general formula (III) and (B3) isoparaffin hydrocarbon oils having a boiling point in the range from 60 to 260° C. under normal pressure.

In the general formula (II), in which $R^1$ and $R^2$ each have the same meaning as defined for the formula (I), representing the component (B1), which has a viscosity not exceeding 1000 centistokes at 25° C., the subscripts p and q are each, independently from the other, 0 or a positive integer not exceeding 500 with the proviso that p+q does not exceed 500. When either of p and q has a value exceeding 500, a decrease is caused in the miscibility of the component (B1) with the component (A) as the film-forming ingredient in the composition. It is preferable that each of the subscripts p and q does not exceed 300 and the viscosity of the component (B1) does not exceed 500 centistokes at 25° C.

The component (B2), which is alternative to the component (B1) described above, is a cyclic organopolysiloxane oligomer represented by the general formula (III) given above, in which $R^1$ and $R^2$ each have the same meaning as defined above and each of the subscripts x and y has a value of 0 or a positive integer not exceeding 7, independently from the other, with the proviso that x+y is 3 to 7. In particular, it is preferable that, when the fluorine content in the component (A) as the film-forming ingredient is in the range from 1 to 20% by weight, y is 0 and x is 3 to 7 or, more preferably, x is 4 or 5. When the fluorine content in the component (A) is in the range from 20 to 50% by weight, it is preferable that x is 0 and y is 3 to 7 or, more preferably, y is 4 or 5.

The component (B3), which is further alternative to the components (B1) and (B2), is an isoparaffin hydrocarbon oil having a boiling point in the range from 60 to 260° C. under normal pressure. When an isoparaffin hydrocarbon oil having a boiling point lower than 60° C. is used as the component (B), the composition compounded therewith is not suitable as an additive in a toiletry or cosmetic preparation due to the strong unpleasant odor of hydrocarbon solvents while, when the boiling point thereof is too high, the miscibility of such an isoparaffin hydrocarbon oil with the component (A) is not good enough. Commercial products of isoparaffin hydrocarbon oils are available under various tradenames including Isopars C, E, G, H, L and M (each a product by Exxon Co.), IP Solvents 1016, 1620 and 2028 (each a product by Idemitsu Petrochemical Co.), Marukazol R (a product by Maruzen Petrochemical Co.), Nisseki Isosols 300 and 400 (each a product by Nippon Petrochemical Co.), Shellsol 71 (a product by Shell Chemical Co.) and Solutols 100, 130 and 220 (each a product by Philip Co.) as well as isohexadecane supplied, for example, by Bayer Japan Co.

The silicone-based film-forming composition of the invention comprises the high-molecular diorganopolysiloxane as the component (A) and the component (B), which is selected from the components (B1), (B2) and (B3), in such a weight proportion that the weight fraction of the component (A) is in the range from 0.5 to 80% or, preferably, from 5 to 30% and the weight fraction of the component (B) is in the range from 20 to 99.5% or, preferably, from 70 to 95%, the total amount of the components (A) and (B) being 100%. When the weight fraction of the component (A) is too low, a coating film having a sufficiently high strength cannot be obtained from the composition while, when the weight fraction of the component (A) is too high, an undue increase is caused in the viscosity of the composition compounded from these two components. It is of course optional that each of the components (A) and (B) is a combination of two kinds or more of the compounds each satisfying the definition of the respective components.

The above described silicone-based film-forming composition can be used as an additive ingredient in a toiletry or cosmetic preparation or, in particular, in a hair care treatment composition which is formulated with (a) from 0.1 to 50% by weight of a surface active agent, (b) from 0.1 to 20% by weight of the silicone-based film-forming composition described above and (c) from 1 to 95% by weight of water and/or ethyl alcohol, the balance, if any, of the components (a), (b) and (c) being other ingredients known in the formulation of the respective preparations for a particular application. When the amount of the component (b) is too small, the hair care treatment composition cannot exhibit full protective effects on the hair treated therewith while, when the amount thereof is too large, a difficulty is encountered in the compounding work of the component (b) with the other ingredients. When the amount of the component (a) is too small, good interface properties necessary for compounding of the ingredients cannot be obtained while, when the amount of the component (a) is too large, the dispersibility of the component (b) in the hair care treatment composition is decreased.

The surface active agent as the component (a) is not particularly limitative relative to the types of ionic surface activity including anionic, amphoteric, cationic and non-ionic surface active agents. Particular examples of the anionic surface active agents include fatty acid soaps, salts of α- acylsulfonic acids, salts of alkylsulfonates, salts of alkylaryl or alkylnaphthalene sulfonates, salts of an addition product of alkyl or alkenyl ether sulfates with ethylene oxide and/or propylene oxide, salts of alkylamide sulfates, salts of alkylamide phosphates, salts of alkyloyl alkyl taurines and salts of N-(long chain acyl)amino carboxylic acids.

Particular examples of the amphoteric surface active agents include carboxy betaine compounds, sulfobetaine compounds, amidobetaine compounds, salts of aminocarboxylic acids and imidazoline compounds.

Particular examples of the cationic surface active agents include quaternary ammonium salts such as cetyl trimethyl ammonium chloride, stearyl trimethyl ammonium chloride, behenyl trimethyl ammonium chloride and stearyl dimethyl benzyl ammonium chloride, amine compounds such as stearamidopropyl dimethyl amine, diethyl aminoethyl stearamide, dimethyl stearamine and myristyl amine, and salts of amines such as stearylamine hydrochloride and stearylamine formate.

Particular examples of the non-ionic surface active agents include addition products of alkyl or alkenyl ethers with ethyleneoxide and/or propyleneoxide, alkylaryl polyoxyethylene ethers, alkylolamides, polyoxyethylene ethers of alkyl glycerin ether type, polyoxyethylene ethers of propyleneglycol esters, polyoxyethylene fatty acid esters, polyoxyethylene ethers of glycerin-fatty acid esters, polyoxyethylene ethers of sorbitan fatty acid esters, fatty acid esters of sorbitol polyoxyethylenes, saccharose fatty acid esters, polyoxyethylene-modified hardened castor oil, polyoxyethylene cholesteryl ethers and polyether-modified silicones.

Besides the essential ingredients, i.e. components (a), (b) and (c), the toiletry or cosmetic preparation of the invention can be admixed, according to the particularly intended application of the preparation, with various kinds of known additives including oily compounds such as liquid paraffins, squalane, lanolin derivatives, higher alcohols and various kinds of ester oils, water-soluble polyhydric alcohols such as ethyleneglycol, propyleneglycol, 1,3-butyleneglycol, glycerin, sorbitol and polyethyleneglycol, moisturizing agents such as hyaluronic acid, chondroitin sulfate and salts of pyrrolidone carboxylic acids, ultraviolet absorbers, ultraviolet diffusers, resins such as acrylic resins, silicone resins and polyvinyl pyrrolidones, proteins and decomposition products of proteins, antiseptic agents such as ethyl paraoxybenzoate and butyl paraoxybenzoate, antioxidants such as di-tert-butyl hydroxytoluene, thickening agents such as carboxy vinyl polymers, perfumes, pigments, dyes and so on.

The forms of the toiletry or cosmetic preparation according to the invention are not particularly limitative including solutions, emulsions, powder dispersions and aerosols. The types of application of the preparation include hair care treatment compositions such as shampoos, hair rinses, hair treatments, hair conditioners, hair oils, hair blow agents, hair lotions and hair sprays, as well as skin care and makeup preparations such as foundations, lip sticks, makeup bases, mascaras, skin creams, skin lotions, sun screen oils and milky lotions.

In the following, the present invention is described in more detail by way of Examples of the silicone-based film-forming compositions and Formulations of toiletry or cosmetic preparations, which, however, never limit the scope of the invention in any way. In the following Examples, characterization of the high-molecular silicones as the component (A) was performed for the average molecular weight measured by using a light-scattering photometer giving an absolute value of the molecular weight and for the contents of fluorine and nitrogen by the conventional method of elemental analysis. In the following, the values of viscosity are all those obtained by the measurement at 25° C. The term of "parts" always refers to "parts by weight" and the term of "%" in the formulations of the toiletry and cosmetic compositions given below always refers to "% by weight".

EXAMPLE 1

A high-molecular diorganopolysiloxane as the component (A), referred to as the polymerizate 1 hereinafter, was prepared by mixing 414 g of octamethyl cyclotetrasiloxane, 0.16 g of hexamethyl disiloxane and 179 g of 1,3,5-trimethyl-1,3,5-tri(3,3,3-trifluoropropyl)cyclotrisiloxane and heating the mixture in the presence of an alkali catalyst followed by neutralization of the alkali catalyst and distillation to remove the unreacted starting materials. The thus obtained organopolysiloxane had a molecular weight of 594,000 and a content of fluorine of 11.0% by weight so that this product could be assumed to be a polymer expressed by the formula

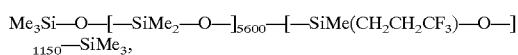

in which Me is a methyl group.

A silicone-based film-forming composition, referred to as the composition 1 hereinafter, which was a clear and colorless liquid, was prepared by mixing 10 parts of the above obtained fluorine-containing diorganopolysiloxane and 90 parts of an isoparaffin oil Nisseki Isosol 4000 (supra).

EXAMPLE 2

A high-molecular diorganopolysiloxane as the component (A), reerred to as the polymerizate 2 hereinafter, was prepared in the same manner as in the preparation of the polymerizate 1 from 274 g of octamethyl cyclotetrasiloxane, 0.16 g of hexamethyl disiloxane and 275 g of 1,3,5-trimethyl-1,3,5-tri(3,3,3-trifluoropropyl)cyclotrisiloxane. The thus obtained diorganopolysiloxane had a molecular weight of 548,000 and a content of fluorine of 18.3% by weight so that this product could be assumed to be a polymer expressed by the formula

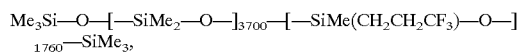

in which Me is a methyl group.

A silicone-based film-forming composition, referred to as the composition 2 hereinafter, which was a clear and colorless liquid, was prepared by mixing 10 parts of the above obtained fluorine-containing diorganopolysiloxane and 90 parts of decamethyl cyclopentasiloxane.

EXAMPLE 3

A high-molecular diorganopolysiloxane as the component (A), referred to as the polymerizate 3 hereinafter, was prepared in the same manner as in the preparation of the polymerizate 1 from 237 g of octamethyl cyclotetrasiloxane, 0.16 g of hexamethyl disiloxane and 390 g of 1,3,5-trimethyl-1,3,5-tri(3,3,3-trifluoropropyl)cyclotrisiloxane. The thus obtained diorganopolysiloxane had a molecular weight of 627,000 and a content of fluorine of 22.7% by weight so that this product could be assumed to be a polymer expressed by the formula

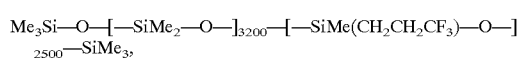

in which Me is a methyl group.

A silicone-based film-forming composition, referred to as the composition 3 hereinafter, which was a clear and colorless liquid, was prepared by mixing 10 parts of the above obtained fluorine-containing diorganopolysiloxane and 90 parts of 1,3,5,7-tetramethyl-1,3,5,7-tetra(3,3,3-trifluoropropyl)cyclotetrasiloxane.

EXAMPLE 4

A high-molecular diorganopolysiloxane as the component (A), referred to as the polymerizate 4 hereinafter, was prepared in the same manner as in the preparation of the polymerizate 1 from 467 g of octamethyl cyclotetrasiloxane, 0.25 g of 1,3-bis(3-aminopropyl)-1,1,3,3-tetramethyl disiloxane and 18.7 g of 1,3,5-trimethyl-1,3,5-tri(3-perfluorooctyl propyl)cyclotrisiloxane. The thus obtained diorganopolysiloxane had a molecular weight of 486,000, content of fluorine of 2.4% by weight and content of nitrogen of 0.0058% by weight so that this product could be assumed to be a polymer expressed by the formula

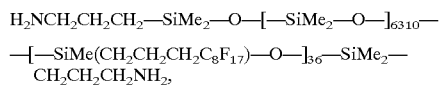

in which Me is a methyl group.

A silicone-based film-forming composition, referred to as the composition 4 hereinafter, which was a clear and colorless liquid, was prepared by mixing 10 parts of the above obtained fluorine- and nitrogen-containing diorganopolysiloxane and 90 parts of a dimethylpolysiloxane oil having a viscosity of 20 centistokes.

EXAMPLE 5

A high-molecular diorganopolysiloxane as the component (A), referred to as the polymerizate 5 hereinafter, was prepared in the same manner as in the preparation of the polymerizate 1 from 366 g of octamethyl cyclotetrasiloxane, 0.16 g of hexamethyl disiloxane, 1105 g of 1,3,5-trimethyl-1,3,5-tri(2-perfluorobutyl ethyl)cyclotrisiloxane and 1.40 g of 1,3,5,7-tetramethyl-1,3,5,7-tetra(3-aminopropyl) cyclotetrasiloxane. The thus obtained diorganopolysiloxane had a molecular weight of 1,470,000, content of fluorine of 41.9% by weight and content of nitrogen of 0.01 14% by weight so that this product could be assumed to be a polymer expressed by the formula

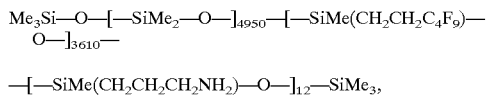

—[—SiMe(CH$_2$CH$_2$CH$_2$NH$_2$)—O—]$_{12}$—SiMe$_3$, in which Me is a methyl group.

A silicone-based film-forming composition, referred to as the composition 5 hereinafter, which was a clear and colorless liquid, was prepared by mixing 10 parts of the above obtained fluorine- and nitrogen-containing diorganopolysiloxane and 90 parts of 1,3,5,7,9-pentamethyl-1,3,5,7,9-penta(3,3,3-trifluoropropyl)cyclopentasiloxane.

EXAMPLE 6

A high-molecular diorganopolysiloxane as the component (A), referred to as the polymerizate 6 hereinafter, was prepared in the same manner as in the preparation of the polymerizate 1 from 445 g of octamethyl cyclotetrasiloxane, 0.16 g of hexamethyl disiloxane, 403 g of a fluorine-containing cyclic siloxane trimer of the formula {SiMe[CH$_2$CH$_2$CH$_2$C(CF$_3$)$_2$(CF$_2$)$_3$CF$_3$]—O—}$_3$ and 3.84 g of an amino-containing cyclic siloxane tetramer of the formula

[SiMe(CH$_2$CH$_2$CH$_2$NHCH$_2$CH$_2$NH$_2$)—O—]$_4$.

The thus obtained diorganopolysiloxane had a molecular weight of 853,000, content of fluorine of 27.8% by weight and content of nitrogen of 0.0788% by weight so that this product could be assumed to be a polymer expressed by the formula Me$_3$Si—O—[—SiMe$_2$—O—]$_{6020}$—

—{—SiMe[CH$_2$CH$_2$CH$_2$C(CF$_3$)$_2$(CF$_2$)$_3$CF$_3$]—O—}$_{960}$—

—[—SiMe(CH$_2$CH$_2$CH$_2$NHCH$_2$CH$_2$NH$_2$)—O—]$_{24}$—SiMe$_3$, in which Me is a methyl group.

A silicone-based film-forming composition, referred to as the composition 6 hereinafter, which was a clear and colorless liquid, was prepared by mixing 10 parts of the above obtained fluorine- and nitrogen-containing diorganopolysiloxane and 90 parts of a fluorine-modified dimethylpolysiloxane oil of the formula Me$_3$Si—O—(—SiMe$_2$—O—)$_{16}$—[—SiMe(CH$_2$CH$_2$CF$_3$)—O—]$_{18}$—SiMe$_3$, in which Me is a methyl group.

Following tests were undertaken for the polymerizates 1 to 6 and the compositions 1 to 6 described above. Solubility test of the polymerizates in various solvents:

Each of the polymerizates 1 to 6 prepared in the above described Examples 1 to 6, respectively, was added to a solvent specified below in a weight proportion of 1:9 and, after agitation for 12 hours at room temperature, the solubility behavior of the polymerizate was visually inspected to record the results in three ratings of A, B and C according to the following criteria of: A for a uniform and clear solution; B for a uniform dispersion; and C for separation into layers. Incidentally, a high-molecular dimethylpolysiloxane oil of the formula Me$_3$Si—O—(—SiMe$_2$—O—)$_{6000}$—SiMe$_3$ could be uniformly dissolved in all of the solvents tested.

Solvent 1: decamethyl cyclopentasiloxane
Solvent 2: dimethyl silicone oil having a viscosity of 20 centistokes
Solvent 3: isoparaffin (Nisseki Isosol 400, supra)
Solvent 4: isooctoic acid triglyceride
Solvent 5: isopropyl palmitate
Solvent 6: cetyl isooctoate

TABLE 1

|  | Polymerizate | | | | | |
| --- | --- | --- | --- | --- | --- | --- |
|  | 1 | 2 | 3 | 4 | 5 | 6 |
| Solvent 1 | A | A | C | A | C | C |
| Solvent 2 | C | C | C | A | C | C |
| Solvent 3 | A | C | C | A | C | C |
| Solvent 4 | C | C | C | B | C | C |
| Solvent 5 | C | C | C | B | C | C |
| Solvent 6 | C | C | C | B | C | C |

Slipperiness Test

A 4 cm by 10 cm wide cowhide was uniformly coated with a 1 g portion of one of the compositions 1 to 6 prepared in Examples 1 to 6, respectively, and, after drying at 50° C. for 24 hours, evaluation of surface slipperiness of the leather pieces before and after coating and drying was conducted by measuring the horizontal sliding resistance by using the PM meter (manufactured by Kyowa Chemical Co.) under conditions of a vertical load of 50 g and pen-point moving velocity of 19 cm/minutes. The results are shown in Table 2 below in the unit of grams. References 1 and 2 shown in the table are the results obtained with a 1:9 by weight mixture of the same high-molecular dimethylpolysiloxane oil as used in the above described solubility test and decamethyl cyclopentasiloxane, and a 1:9 by weight mixture of an amino-modified dimethylpolysiloxane oil of the formula Me$_3$Si—O—(—SiMe$_2$—O—)$_{6000}$—[—SiMe(CH$_2$CH$_2$CH$_2$NH$_2$)—O—]$_{10}$—SiMe$_3$ and decamethyl cyclopentasiloxane, respectively. It is clear from the results shown in the table that the silicone-based film-forming compositions according to the invention each exhibit excellent slipperiness as compared with conventional silicones.

TABLE 2

|  | Composition | | | | | | Reference | |
| --- | --- | --- | --- | --- | --- | --- | --- | --- |
|  | 1 | 2 | 3 | 4 | 5 | 6 | 1 | 2 |
| before coating | 26.3 | 27.9 | 28.1 | 27.2 | 27.4 | 28.3 | 27.7 | 27.4 |
| as coated | 13.6 | 12.0 | 11.7 | 14.9 | 10.6 | 11.0 | 19.5 | 19.0 |

Water Resistance Test

Three sun screen oil preparations, referred to as the oils 1, 2 and 3 hereinafter, were prepared in the following formulations. Thus, the oil 1 was formulated with 20% of a high-molecular dimethyl silicone composition, which was 1:9 by weight mixture of the same dimethylpolysiloxane oil as used in the solubility test described above and decamethyl cyclopentasiloxane, 5% of liquid paraffin, 25% of decamethyl cyclopentasiloxane and 50% of ethyl alcohol. The formulations of the oils 2 and 3 were each the same as the formulation of the oil 1 excepting for the replacement of the high-molecular dimethyl silicone composition with the same amount of the composition 1 or 2, respectively.

A 5 cm by 5 cm wide glass plate uniformly coated with 1.0 g of one of the oils 1 to 3 was, after drying at 50° C. for 24 hours, held standing at an inclination angle of about 45 degrees and the coated surface was exposed to a flushing water stream for 5 minutes. After thorough drying to remove water drops, the glass plate was weighed to determine the remaining weight of the coating layer. The results were that the coating layers of the oils 1, 2 and 3 retained 74%, 92% and 96%, respectively, of the weight before the water flushing. These results indicate that the film-forming composition according to the invention can exhibit greatly improved water resistance as compared with conventional silicones.

Formulation 1

Four shampoo compositions, referred to as the shampoos 1 to 4, respectively, hereinafter, were prepared in the following formulation. Thus, the shampoo 1 was prepared by blending 20% of sodium dodecyl sulfate, 2% of a 1:9 by weight mixture of the same high-molecular dimethylpolysiloxane oil as used in the solubility test above and decamethyl cyclopentasiloxane and 78% of water. The formulations of the shampoos 2, 3 and 4 were each the same as above excepting for the replacement of the high-molecular dimethylpolysiloxane oil/decamethyl cyclopentasiloxane mixture with the same amount of the composition 1, 2 or 4, respectively, prepared in Examples 1, 2 and 4.

These shampoo compositions were subjected to the evaluation test for the glossiness and smoothness of combing of the hair shampooed therewith and after rinse or after drying by 10 panel members, each member recording the results in 5-point ratings of 5 (excellent), 4 (good), 3 (fairly good), 2 (somewhat poor) and 1 (poor). The results recorded by the panel members were averaged and shown in Table 3 by four ratings of: A for at least 4.5 points, B for 3.5 to 4.5 points. C for 2.5 to 3.5 points and D for lower than 2.5 points.

TABLE 3

|  |  | Shampoo | | | |
|---|---|---|---|---|---|
|  |  | 1 | 2 | 3 | 4 |
| Glossiness | after rinse | C | B | B | A |
|  | after drying | B | A | A | A |
| Combing | after rinse | B | A | A | A |
| Smoothness | after drying | C | B | B | A |

Formulation 2

A hair conditioning agent was prepared by blending:
0.50% of hydroxyethyl cellulose;
2.00% of stearyl trimethyl ammonium chloride;
0.50% of a polyether-modified silicone (KF 601, a product by Shin-Etsu Chemical Co.);
1.50% of stearyl alcohol;
0.50% of stearamidopropyl dimethyl amine;
1.00% of glycerin monostearate;
1.00% of the composition 2; and
93.0% of deionized water.

Formulation 3

A hair rinse composition was prepared by blending:
1.00% of cetyl trimethyl ammonium chloride;
2.00% of cetyl alcohol;
2.00% of the composition 3;
1.50% of glycerin monostearate;
0.50% of stearic acid;
5.00% of glycerin;
5.00% of propyleneglycol; and
83.0% of deionized water.

Formulation 4

A hair spray composition was prepared by blending:
10.0% of the composition 5;
1.00% of a polyether-modified silicone (KF 6015, a product by Shin-Etsu Chemical Co.);
5.00% of ethyl alcohol; and
84.0% of dimethyl ether.

Formulation 5

A hair cream composition was prepared by blending:
15.0% of the composition 6;
5.00% of a dimethylpolysiloxane oil having a viscosity of 20 centistokes;
8.00% of glycerin tri(2-ethylhexoate);
5.00% of petrolatum;
2.00% of stearyl alcohol;
2.00% of sorbitan monooleate;
2.00% of hardened castor oil ester of polyoxyethylene (40);
5.00% of glycerin; and
56.0% of deionized water.

Formulation 6

A hair blow agent was prepared by blending:
5.00% of the composition 2;
2.00% of 1,3-butyleneglycol;
2.00% of hardened castor oil ester of polyoxyethylene (60);
15.0% of ethyl alcohol; and
76.0% of deionized water.

Formulation 7

A hair setting agent was prepared by blending:
10.0% of the composition 3;
1.00% of trimethylsiloxy silicate (KF 7312F, a product by Shin-Etsu Chemical Co.);
3.00% of glycerin;
2.00% of hardened castor oil ester of polyoxyethylene (120);
15.0% of ethyl alcohol;
61.0% of deionized water; and
8.00% of n-butane.

Formulation 8

A foundation was prepared by blending:
31.0% of decamethyl cyclopentasiloxane;
2.00% of dimethylpolysiloxane oil having a viscosity of 6 centistokes;
2.00% of the composition 4;
2.00% of hohoba oil;
8.00% of ceresine;
1,00% of microcrystalline wax;
2.00% pg a polyether-modified silicone (KF 6017, a product by Shin-Etsu Chemical Co.)

20.0% of hydrophobilized pigment powder;
10.0% of deionized water;
1.00% of sodium L-glutamate;
15.0% of glycerin: and
6.00% of propyleneglycol.

Formulation 9

A lip stick composition was prepared by blending:
15.0% of octamethyl cyclotetrasiloxane;
30.0% of a dimethylpolysiloxane oil having a viscosity of 6 centistokes;
2.00% of the composition 5;
3.00% of carnauba wax;
13.0% of aristo wax (165 F);
2.00% of a polyether-modified silicone (KF 6017, supra);
0.50% of red iron oxide;
1.00% of yellow iron oxide;
1.00% of red pigment;
11.0% of titanium dioxide;
4.00% of deionized water;
17.0% of glycerin; and
0.50% of atherocollagen.

Formulation 10

A sun screen composition was prepared by blending:
28.5% of deionized water;
1.00% of sodium pyrrolidone carboxylate:
2.00% of the composition 6;
1.50% of sodium L-glutamate;
15.0% of propyleneglycol:
0.50% of cetanol;
0.50% of stearic acid;
15.0% of decamethyl cyclopentasiloxane;
3.00% of liquid paraffin having a viscosity of 70 centistokes;
2.00% of olive oil;
5.00% of a polyether-modified silicone (KF 6017, supra);
1.00% of lanolin;
5.00% of titanium dioxide;
9.00% of sericite;
5.00% of zinc oxide;
0.50% of yellow iron oxide;
0.50% of red iron oxide; and
5.00% of nylon powder.

What is claimed is:

1. A film-forming silicone-based composition which comprises, as a uniform mixture:
   (A) from 0.5 to 80% by weight of a diorganopolysiloxane having a straightly linear molecular structure represented by the formula

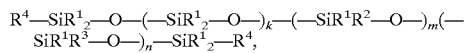

in which $R^1$ is an alkyl group, cycloalkyl group or aryl group having 1 to 20 carbon atoms wherein $R^1$ are at least 90% methyl groups, $R^2$ is a fluorine-substituted alkyl group having 1 to 15 carbon atoms, $R^3$ is an amino- or ammonium-functional organic group represented by the formula $—R^5Z$, $R^5$ being an alkylene group having 2 to 6 carbon atoms and Z being a group of the formula $—NR^6{}_2$, $—N^+R^6{}_3A—$, $—NR^6(CH_2)_aNR^6{}_2$ or $—NR^6(CH_2)_aN^+R^6A^-$ with the proviso that $R^6$ is a hydrogen atom or an alkyl group having 1 to 4 carbon atoms, A is a halogen atom and the subscript a is an integer of 2 to 6, $R^4$ is $R^1$, $R^2$, $R^3$ or a hydroxyl group, the subscripts k and m are each, independently from the other, a positive integer and the subscript n is 0 or a positive integer with the proviso that k+m+n is in the range from 2000 to 20,000, of which the content of nitrogen does not exceed 1% by weight and the content of fluorine is in the range from 1% to 50% by weight; and (B) from 20 to 99.5% by weight of an oily compound selected from the group consisting of:
   (B1) a diorganopolysiloxane having a straightly linear molecular structure represented by the formula

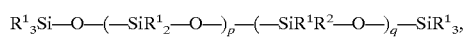

in which $R^1$ and $R^2$ each, independently from the other, have the same meaning as defined above and the subscripts p and q each, independently from the other, are 0 or a positive integer not exceeding 500 with the proviso that p+q does not exceed 500, and having a viscosity not exceeding 1000 centistokes at 25° C.;
   (B2) a cyclic diorganosiloxane oligomer represented by the formula

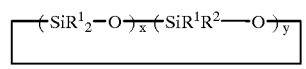

in which $R^1$ and $R^2$ each, independently from the other, have the same meaning as defined above and the subscripts x and y are each, independently from the other, 0 or a positive integer not exceeding 7 with the proviso that x+y is a positive integer in the range from 3 to 7; and
   (B3) an isoparaffin hydrocarbon compound having a boiling point in the range from 60 to 260° C. under normal pressure, the total amount of the components (A) and (B) being 100% by weight.

2. The film-forming silicone-based composition as claimed in claim 1 in which, in the general formula representing the component (A), the subscript n is 0 and the group denoted by $R^4$ is $R^1$, $R^2$ or a hydroxyl group.

3. The film-forming silicone-based composition as claimed in claim 1 in which the content of fluorine in the component (A) is in the range from 1 to 20% by weight.

4. The film-forming silicone-based composition as claimed in claim 1 in which the content of fluorine in the component (A) is in the range from 20 to 50% by weight and the component (B) is selected from the component (B1) and the component (B2) of which, in the general formula representing the component (B2), the subscript x is 0 and the subscript y is in the range from 3 to 7.

5. A toiletry preparation which comprises, as a blend:
   (a) from 0.01 to 50% by weight of surface active agent;
   (b) from 0.01 to 20% by weight of the film-forming silicone-based composition defined in claim 1; and
   (c) from 1 to 95% by weight of water, ethyl alcohol or a combination thereof.

6. The film-forming silicone-based composition of claim 1 wherein $R^2$ is selected from a 2-(perfluoroalkyl)ethyl or 3-(perfluoroalkyl)propyl group.

7. The film-forming silicone-based composition of claim 1 wherein $R^3$ is selected from an amino- or ammonium-functional organic group.

8. The film-forming silicone-based composition of claim 1 wherein the fluorine content in the component (A) is in the range from 1 to 20% by weight.

9. The film-forming silicone-based composition of claim 1 wherein the weight fraction of component (A) is in the range from 5% to 30% and the weight fraction of component (B) is in the range from 70 to 95%.

10. The toiletry preparation of claim 5, further comprising an oily compound, an alcohol, an ester oil, a water-soluble polyhydric alcohol, a moisturizing agent, a salt of pyrrolidone carboxylic acid, an ultraviolet absorber, an ultraviolet diffuser, a resin, a protein, an antiseptic agent, an antioxidant, a thickening agent, a perfume, a pigment, or a dye.

11. The toiletry preparation of claim 5 wherein the surface active agent is selected from an anionic surface active agent.

12. The toiletry preparation of claim 5 wherein the surface active agent is selected from an amphoteric surface active agent.

13. The toiletry preparation of claim 5 wherein the surface active agent is selected from a cationic surface active agent.

14. The toiletry preparation of claim 5 wherein the surface active agent is selected from a non-ionic surface active agent.

15. The film-forming silicone-based composition of claim 1 wherein the content of nitrogen in the diorganopolysiloxane as the component (A) does not exceed 0.5% by weight.

16. A sun screen, a hair conditioning agent, a hair rinse, a hair spray, a hair cream, a hair blow agent, a hair setting agent, a foundation, or a lipstick comprising the film-forming silicone-based composition of claim 1.

17. A film-forming silicone-based composition which comprises, as a uniform mixture:
(A) from 0.5 to 80% by weight of a diorganopolysiloxane having a straightly linear molecular structure represented by the formula

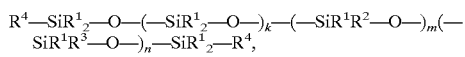

in which $R^1$ is an alkyl group, cycloalkyl group or aryl group having 1 to 20 carbon atoms wherein $R^1$ are at least 90% methyl groups, $R^2$ is a fluorine-substituted alkyl group having 1 to 15 carbon atoms, $R^3$ is an amino- or ammonium-functional organic group represented by the formula $—R^5Z$, $R^5$ being an alkylene group having 2 to 6 carbon atoms and Z being a group of the formula $—NR^6_2$, $—N^+R^6_3A^-$, $—NR^6(CH_2)_aNR^6_2$ or $—NR^6(CH_2)_aN^+R^6A^-$, $R^6$ is a hydrogen atom or an alkyl group having 1 to 4 carbon atoms, A is a halogen atom and the subscript a is an integer of 2 to 6, $R^4$ is $R^1$, $R^2$, $R^3$ or a hydroxyl group, the subscripts k and m are each, independently from the other, a positive integer and the subscript n is a positive integer with the proviso that k+m+n is in the range from 2000 to 20,000, of which the content of nitrogen does not exceed 1% by weight and the content of fluorine is in the range from 1% to 50% by weight; and
(B) from 20 to 99.5% by weight of an oily compound selected from the group consisting of:
(B1) a diorganopolysiloxane having a straightly linear molecular structure represented by the formula

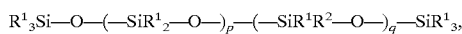

in which $R^1$ and $R^2$ each, independently from the other, have the same meaning as defined above and the subscripts p and q each, independently from the other, are 0 or a positive integer not exceeding 500 with the proviso that p+q does not exceed 500, and having a viscosity not exceeding 1000 centistokes at 25° C.;
(B2) a cyclic diorganosiloxane oligomer represented by the formula

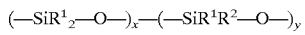

in which $R^1$ and $R^2$ each, independently from the other, have the same meaning as defined above and the subscripts x and y are each, independently from the other, 0 or a positive integer not exceeding 7 with the proviso that x+y is a positive integer in the range from 3 to 7; and
(B3) an isoparaffin hydrocarbon compound having a boiling point in the range from 60 to 260° C. under normal pressure, the total amount of the components (A) and (B) being 100% by weight.

18. A blend comprising:
(a) from 0.1 to 50% by weight of a surface active agent; and
(b) a film-forming silicone-based composition comprising, as a uniform mixture:
(A) from 0.5 to 80% by weight of a diorganopolysiloxane having a straightly linear molecular structure represented by the formula

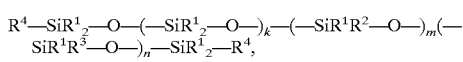

in which $R^1$ is an alkyl group, cycloalkyl group or aryl group having 1 to 20 carbon atoms wherein $R^1$ are at least 90% methyl groups, $R^2$ is a fluorine-substituted alkyl group having 1 to 15 carbon atoms, $R^3$ is an amino- or ammonium-functional organic group represented by the formula $—R^5Z$, $R^5$ being an alkylene group having 2 to 6 carbon atoms and Z being a group of the formula $—NR^6_2$, $—N^+R^6_3A^-$, $—NR^6(CH_2)_aNR^6_2$ or $—NR^6(CH_2)_aN^+R^6A^-$ with the proviso that $R^6$ is a hydrogen atom or an alkyl group having 1 to 4 carbon atoms, A is a halogen atom and the subscript a is an integer of 2 to 6, $R^4$ is $R^1$, $R^2$, $R^3$ or a hydroxyl group, the subscripts k and m are each, independently from the other, a positive integer and the subscript n is 0 or a positive integer with the proviso that k+m+n is in the range from 2000 to 20,000, of which the content of nitrogen does not exceed 1% by weight and the content of fluorine is in the range from 1% to 50% by weight; and
(B) from 20 to 99.5% by weight of an oily compound selected from the group consisting of:
(B1) a diorganopolysiloxane having a straightly linear molecular structure represented by the formula

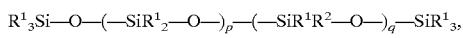

in which $R^1$ and $R^2$ each, independently from the other, have the same meaning as defined above and the subscripts p and q each, independently from the other, are 0 or a positive integer not exceeding 500 with the proviso that p+q does not exceed 500, and having a viscosity not exceeding 1000 centistokes at 25° C.;
(B2) a cyclic diorganosiloxane oligomer represented by the formula

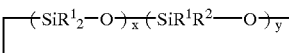

in which $R^1$ and $R^2$ each, independently from the other, have the same meaning as defined above and the subscripts x and y are each, independently from the other, 0 or a positive integer not exceeding 7 with the proviso that x+y is a positive integer in the range from 3 to 7; and (B3) an isoparaffin hydrocarbon compound having a boiling point in the range from 60 to 260° C. under normal pressure, the total amount of the components (A) and (B) being 100% by weight.

19. A toiletry or cosmetic composition, comprising, as a blend:

(a) from 0.1 to 50% by weight of a surface active agent;

(b) a film-forming silicone-based composition comprising, as a uniform mixture:

(A) from 0.5 to 80% by weight of a diorganopolysiloxane having a straightly linear molecular structure represented by the formula

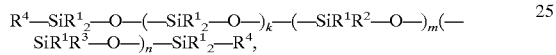

in which $R^1$ is an alkyl group, cycloalkyl group or aryl group having 1 to 20 carbon atoms wherein $R^1$ are at least 90% methyl groups, $R^2$ is a fluorine-substituted alkyl group having 1 to 15 carbon atoms, $R^3$ is an amino- or ammonium-functional organic group represented by the formula —$R^5Z$, $R^5$ being an alkylene group having 2 to 6 carbon atoms and Z being a group of the formula —$NR^6_2$, —$N^+R^6_3A^-$, —$NR^6(CH_2)_aNR^6_2$ or —$NR^6(CH_2)_aN^+R^6A^-$ with the proviso that $R^6$ is a hydrogen atom or an alkyl group having 1 to 4 carbon atoms, A is a halogen atom and the subscript a is an integer of 2 to 6, $R^4$ is $R^1$, $R^2$, $R^3$ or a hydroxyl group, the subscripts k and m are each, independently from the other, a positive integer and the subscript n is a positive integer with the proviso that k+m+n is in the range from 2000 to 20,000, of which the content of nitrogen does not exceed 1% by weight and the content of fluorine is in the range from 1% to 50% by weight; and (B) from 20 to 99.5% by weight of an oily compound selected from the group consisting of:

(B1) a diorganopolysiloxane having a straightly linear molecular structure represented by the formula

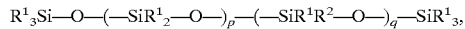

in which $R^1$ and $R^2$ each, independently from the other, have the same meaning as defined above and the subscripts p and q each, independently from the other, are 0 or a positive integer not exceeding 500 with the proviso that p+q does not exceed 500, and having a viscosity not exceeding 1000 centistokes at 25° C.;

(B2) a cyclic diorganosiloxane oligomer represented by the formula

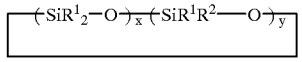

in which $R^1$ and $R^2$ each, independently from the other, have the same meaning as defined above and the subscripts x and y are each, independently from the other, 0 or a positive integer not exceeding 7 with the proviso that x+y is a positive integer in the range from 3 to 7; and (B3) an isoparaffin hydrocarbon compound having a boiling point in the range from 60 to 260° C. under normal pressure, the total amount of the components (A) and (B) being 100% by weight; and (c) from 1 to 95% by weight of water, ethyl alcohol or a combination thereof.

* * * * *